United States Patent [19]

Schmidt

[11] 4,217,544
[45] Aug. 12, 1980

[54] METHOD AND APPARATUS FOR IMPROVED TEMPERATURE COMPENSATION IN A CORROSION MEASUREMENT SYSTEM

[75] Inventor: Thomas R. Schmidt, Houston, Tex.

[73] Assignee: Shell Oil Company, Houston, Tex.

[21] Appl. No.: 951,918

[22] Filed: Oct. 16, 1978

[51] Int. Cl.² .................................................. G01R 27/02
[52] U.S. Cl. .................................. 324/65 CR; 73/86; 23/230 C; 204/195 C
[58] Field of Search ................. 324/65 CR, 71 E; 73/362 AR, 86; 338/13; 23/230 C; 422/53; 204/195 C, 1

[56] References Cited

U.S. PATENT DOCUMENTS

| | | | |
|---|---|---|---|
| 2,824,283 | 2/1958 | Ellison | 23/230 C X |
| 2,987,685 | 6/1961 | Schaschl | 73/86 X |
| 3,047,847 | 7/1962 | Marsh et al. | 324/65 CR |
| 3,094,865 | 6/1963 | Dravnieks et al. | 73/86 |
| 3,102,979 | 9/1963 | Schaschl | 73/86 X |
| 3,104,355 | 9/1963 | Holmes et al. | 73/86 X |
| 3,108,242 | 10/1963 | Scott, Jr. | 338/13 |
| 3,124,771 | 3/1964 | Rohrback | 338/13 |
| 3,156,631 | 11/1964 | Seyl | 204/1 |
| 4,019,133 | 4/1977 | Manley et al. | 324/65 CR |

Primary Examiner—Stanley T. Krawczenwicz

[57] ABSTRACT

An improved method and apparatus to compensate for temperature variations in an electrical resistance corrosion measuring system. Sacrificial probes are inserted into a corrosive atmosphere at significant points, and corrosion-related losses from these probes are measured by monitoring changes in probe resistance. By comparing these changes to a reference probe, accurate determinations of corrosion are made. A novel method of automatic temperature compensation removes essentially all degrading effects of changes in temperature on the corrosion measurement system, by obtaining a reference signal which varies proportionately with temperature and counteracting instantaneous and extended temperature changes by subtracting the reference signal due to temperature variations from the uncompensated system output signal due to the combined effects of corrosion and temperature.

16 Claims, 3 Drawing Figures

METHOD AND APPARATUS FOR IMPROVED TEMPERATURE COMPENSATION IN A CORROSION MEASUREMENT SYSTEM

BACKGROUND OF THE INVENTION

Corrosion measuring and monitoring methods take several forms. Ultrasonic readings, pH monitoring, use of corrosion coupons, and linear polarization methods are only a few of the numerous methods now in existence. One method which has proved useful in measuring corrosion rate is the electrical resistance method, illustrated in U.S. Pat. No. 3,104,355 issued to E. A. Holmes et al in 1963. A particular advantage of the electrical resistance method has been its ability to accurately model corrosion from a particular corrosive environment over a long period of time. Typically, corrosion rate by the electrical resistance method is determined by inserting sacrificial electrical resistance elements, or probes, into a corrosive environment, such as a plant stream, at significant points and measuring actual metal loss from these probes. Measured metal loss from these probes or elements, which are constructed of the same materials as the plant, is an indication of metal being lost by the vessels, piping, etc. of the plant. As the element corrodes, the cross sectional area diminishes, increasing the electrical resistance of the element. The increasing resistance of the corroding active element is compared to a resistance reading from a reference element which is protectively disposed in the corrosive environment, for example, by comparison through such means as a balanced-bridge circuit. Both elements may be constructed out of materials with similar temperature coefficients, so the comparison provides some automatic temperature compensation to the corrosion measurement system. The principle being utilized is that, as the temperature of the environment changes, the corresponding resistance change of the reference element nullifies the resistance change of the active element due to temperature. This particular method of temperature compensation is more fully described in U.S. Pat. No. 3,104,335, previously referenced. The resistance of the element, after being partially compensated for temperature variation, is directly proportional to a corrosion dial reading. By plotting these dial readings over an extended period of time, for instance two weeks, a slope may result which corresponds to an average corrosion rate over that period of time. The resistance elements used as probes may be used in a number of environments and are available in a variety of alloys, each alloy corresponding with the particular metal whose loss is being determined.

The basic problem with corrosion rate determination by the electrical resistance method has been the inability to accurately measure the slight amounts of metal lost per hour or even per day, even though the cumulative effect over a longer period, such as one year, may be unacceptable. Metal losses for usual corrosion rates are on the order of millionths of an inch per hour with corresponding changes in probe resistance of tenths of a micro-ohm. The problem of accurately determining small amounts of corrosion resolves itself into one of a signal-to-noise ratio in which the "signal" to be preserved and enhanced is the change in probe resistance due to metal loss and the "noise" to be reduced is the composite of many extraneous effects, i.e., temperature, line voltage, and electrical pick up.

Heretofore, these extraneous effects causing "noise" have limited the use of the electrical resistance method to a time-average system of corrosion measurement as opposed to a real time "instantaneous" corrosion measurement, since the best time resolution possible has been one to two weeks. Hence, successive readings of corrosion loss in units of inches of penetration are taken, and by dividing the inches of penetration by the time interval (typically one to two weeks) and applying the proper conversion factors, an average corrosion rate in mils per year (MPY-thousandths of an inch per year) may be calculated. While the probes may be designed using a reference element to provide temperature compensation, temperature effects remain as the single largest source of extraneous fluctuation or noise in the system. For instance, ° C. (centigrade) temperature change of the active resistance element has about 100 times the effect on probe resistance as corrosion for one hour at a 10 MPY rate. This may be partially compensated by a reference element, but a residual offset and resulting temperature effect, caused by such things as variations in manufacturing of the elements and minute variations in composition of the elements, exists in the active-reference element system. In addition to this residual imbalance effect which exists even when the active and reference element are at the same temperature, any difference in temperature between the elements, such as occurs during temperature changes of the corrosive atmosphere, will cause an even more pronounced imbalanced transient effect. The time-average method and apparatus for corrosion measurement is illustrated in U.S. Pat. No. 3,094,865 issued to Dravnieks et al in 1963, and U.S. Pat. No. 3,104,355, discussed above.

SUMMARY OF THE INVENTION

The present invention solves the problems associated with the electrical resistance corrosion measurement systems now in use by providing overall noise compensation, thus increasing the signal-to-noise ratio to a point where the system may be used as a real time corrosion rate determination device. One especially important aspect of the invention involves utilizing a temperature measuring device to provide a compensating signal for eliminating all degrading temperature effects from the corrosion measurement system.

BRIEF DESCRIPTION OF THE DRAWING

Other advantages and capabilities of the present invention will become apparent from the following detailed description of the preferred embodiments when taken in conjunction with the attached drawing, in which.

DESCRIPTION OF THE PREFERRED EMBODIMENT

Figure 1:
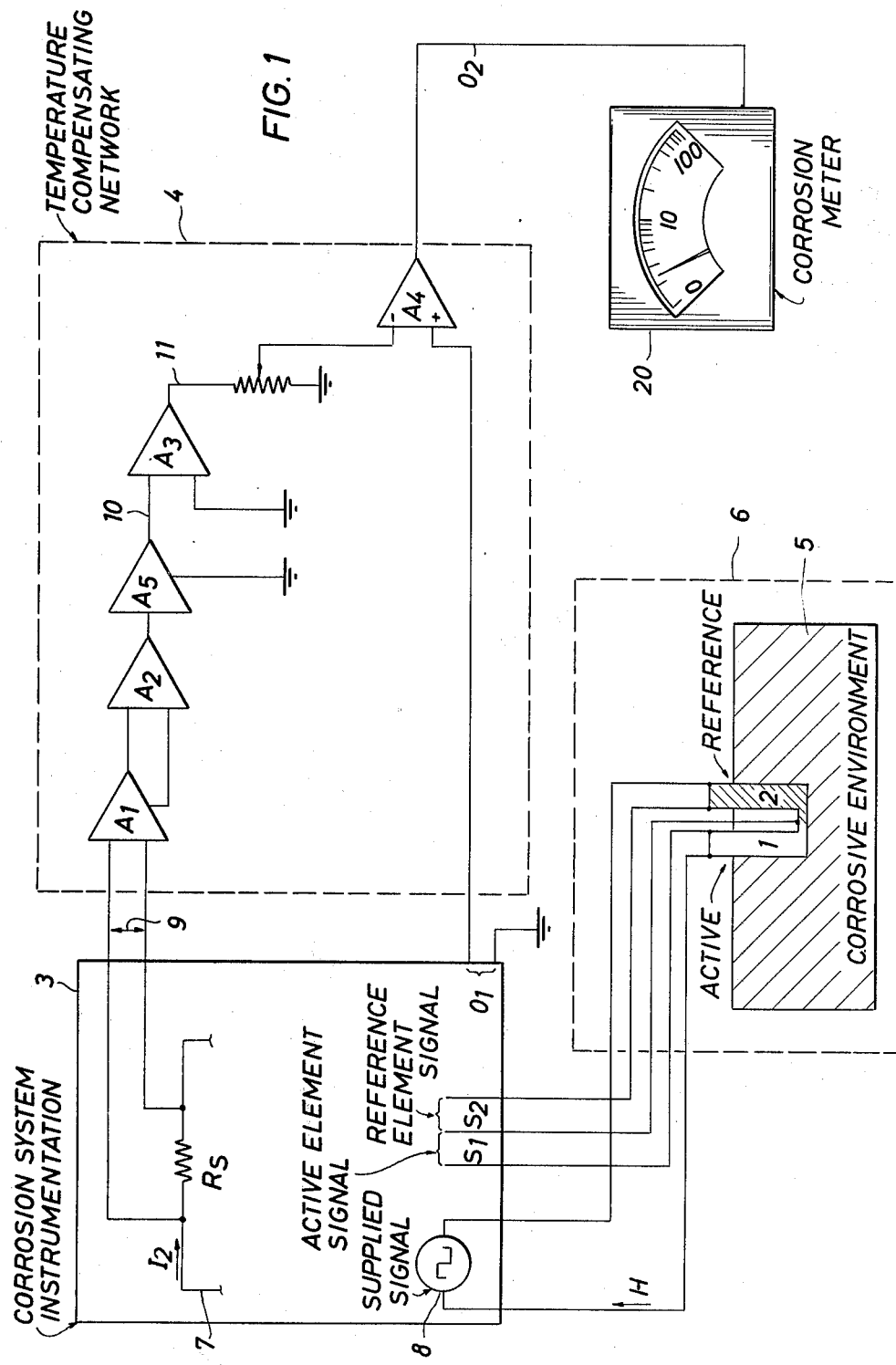
FIG. 1 is a simplified schematic showing the temperature compensating feature of the present invention.

The first step in providing complete compensation to a corrosion measurement system for variations in the temperature of the corrosive atmosphere as taught by the present invention involves obtaining an electrical signal that varies proportionately with the temperature of the corrosive atmosphere. This signal provides the basis for a reference signal against which the extent of corrosion of an electrical resistance element disposed in the corrosive atmosphere may be measured. The reference signal is particularly useful in combination with an uncompensated output from a typical electrical resistance corrosion measurement system, wherein electrical resistance elements are inserted into the corrosive atmosphere. Electrical instrumentation, such as a transformer or a power source, may be utilized to provide a generated signal (such as current or voltage) in the resistance elements. Various electrical measuring means may be used to sense changes in the signals generated in the resistance elements. These changes may be caused by corrosion of the resistance elements, and, to a large extent, the temperature of the corrosive atmosphere. As resistance element corrosion proceeds, the resistance of the elements would tend to increase, due to the decrease in their cross-sectional area. However, a large apparent change in resistance, which may partially or completely offset the change due to corrosion or may enhance the change due to corrosion, will appear due to the temperature of the corrosive atmosphere. In the present invention, a temperature sensing device, such as a thermometer, thermocouple, or resistance thermometer, is used to provide an electrical signal proportional only to temperature variations of the corrosive atmosphere, which becomes the reference against which system corrosion is measured. Ideally, the temperature sensing device is disposed in as close proximity as possible to the resistance element, in order to sense the temperature variations of the resistance element. For instance, a thermocouple could be attached to a protected surface of the active (corroding) resistance element. Through appropriate calibration and balancing procedures performed on the electrical resistance element, it may be determined what fractional portion of the generated signal is due to temperature effects, so that the reference signal may be used to offset this fractional portion. A subtractor circuit may be utilized to combine the uncompensated system output due to the generated signal in the resistance element and the reference signal such that the net resulting output is independent of fluctuation due to temperature variations of the corrosive atmosphere. In some instances, it will be necessary to reduce or increase the magnitude of the reference signal by appropriate scaling, so that it will have the proper offsetting effect on the uncompensated system output. This final trimming, which is necessary to arrive at the compensated system output, can be accomplished as part of the overall system calibration.

One particularly useful embodiment of the present invention involves taking a supplied signal from the electrical instrumentation associated with the corrosion measurement system, which signal may be a driving voltage or current, and electrically combining it with the measurable signal it induces across the noncorroding reference element. As the temperature varies, the apparent thickness of the reference element changes due to a temperature-induced change in resistance. Since no corrosion or erosion of the reference element can occur, the change in resistance becomes a measure of change in temperature. By monitoring the induced signal across the reference element and making the appropriate comparison with the inducing, driving signal, the reference element becomes a resistance thermometer. One method of making this comparison is to maintain at a constance level a voltage signal induced across the reference element by varying the drive current. This method is being accomplished in some presently existing corrosion measurement systems, for instance the Magna Instruments, Inc., Corrosometer System, but for other reasons than for providing a resistance thermometer. The varying drive current, then, becomes a signal which varies proportionately with the temperature.

Referring now to FIG. 1, an electrical resistance corrosion measurement system is shown composed of the corrosion system instrumentation 3, the electrical resistance elements 1 and 2 disposed in a corrosive environment 5, and the temperature compensation network 4. In one embodiment of the invention, a pair of electrically conducting elements 1 and 2 are in the form of two resistances connected in series, the active element 1 being exposed to the corrosive environment 5 and the reference element 2 being protected therefrom. A supplied signal 8, in this instance a periodically varying current $I_1$, induces measurable signals $S_1$ and $S_2$ across resistance elements 1 and 2, respectively. When the supplied signal 8 is a current signal, the induced measurable signals $S_1$ and $S_2$ will be voltage signals. As the active element 1 corrodes or erodes in some manner, its resistance changes due to a reduction in cross-sectional area, and measurable signal $S_1$ varies proportionately to the corrosion of element 1. Reference element 2, on the other hand, although disposed in the corrosive environment 5, is protected from corrosion. In this way, element 2 and element 1 are exposed to substantially the same temperatures. If element 2 cannot corrode, any change induced in signal $S_2$ must be due to a change in temperature of the corrosive environment. By combining supplied signal 8 and measurable signal $S_2$, a composite signal may result which varies directly with temperature of environment 5. For instance, by varying supplied signal 8 to maintain measurable signal $S_2$ constant, the variations in supplied signal 8 correspond to variations in temperature. A reference signal 9 may be obtained by sampling any signal, a current signal in this instance, which is directly proportional to supplied signal 8. A sampling resistor may be serially placed in a current line 7, in which current $I_2$ is directly proportional to supplied current $I_1$. The reference signal 9, a voltage in this instance, then varies directly with changes in the temperature of environment 5.

In this example, since the reference signal 9 has not been sampled at the base reference at which the uncompensated output $0_1$ exists, a conversion must be made to allow the subsequent combination of the uncompensated corrosion system output $0_1$ and reference signal 9. Operational amplifiers $A_2$ and $A_5$ form an isolation amplifier, isolating signal 9 and converting it to the same ground potential as output $0_1$ and operational amplifier $A_3$ takes this converted signal 10 and transforms it by amplification to a signal at an equivalent to the level of output $0_1$. Equivalent signal 11 and output $0_1$ are then combined in subtractor circuit $A_4$, wherein output $0_1$ is reduced in signal magnitude by equivalent signal 11, and the net resulting output $0_2$ is fully compensated for temperature variations of environment 5. Output $0_2$ may be displayed in real time fashion on a suitable meter, such as galvonometer 20, or it may be processed and permanently recorded as explained below.

Figure 2:
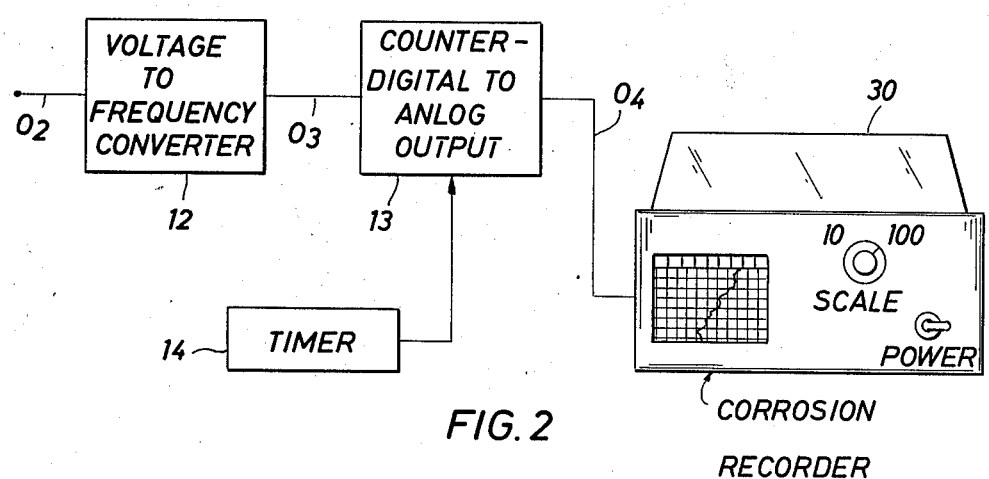
FIG. 2 is a simplified schematic showing the conversion of the compensated output to a coherent, real time output.

An additional method of enhancing the net resulting output $0_2$ of the present invention involves integrating output $0_2$ in order to eliminate any short-term thermal transients that may arise from time to time, making the system useful as a real time device. A one or two hour integration interval is typical, although successful results may be obtained with much shorter intervals. Referring to FIG. 2, output 02, a voltage signal in this instance, is converted to a proportionally varying frequency by voltage to frequency converter 12. For instance, output 03 may be a 0–100 kHz varying frequency signal. Counter 13 accumulates the frequency output 03 for the selectable integration interval. A counter 13 with a digital to analog output may be especially useful to provide an output voltage suitable for interfacing with a plant computer. A number of consecutive digits (for instance 3) stored in the counter may then be converted upon integration to an analog output signal. Timer 14 controls the period of accumulation of signal 03, such that at the conclusion of a timing period, an output voltage proportional to a specified number of consecutive digits is presented as output 04 during the next accumulation period. This signal 04 represents an average thickness of active element 1 of FIG. 1 for the timing interval and the corrosion rate is shown by the slope of these signals, which may be suitably displaced by means such as a strip chart recorder 30.

Additional refinements of the corrosion measurement system may be made to increase the time resolution even further. Room temperature effects on system electrical instrumentation, which may induce an apparent offset equivalent to a corrosion rate of as much as 4.4 MPY for one hour, may be eliminated by installing fans, heaters and thermostatic controls to maintain the internal instrumentation case temperature at a specified level. Additionally, minute variations in the input power may account for an apparent corrosion rate of as much as −5.26 MPY, which can be eliminated by using multiple stages of line voltage regulation. Extraneous signals may also cause erratic interference effects, which signals may be eliminated by providing radio frequency filtering to the electrical instrumentation.

Figure 3:
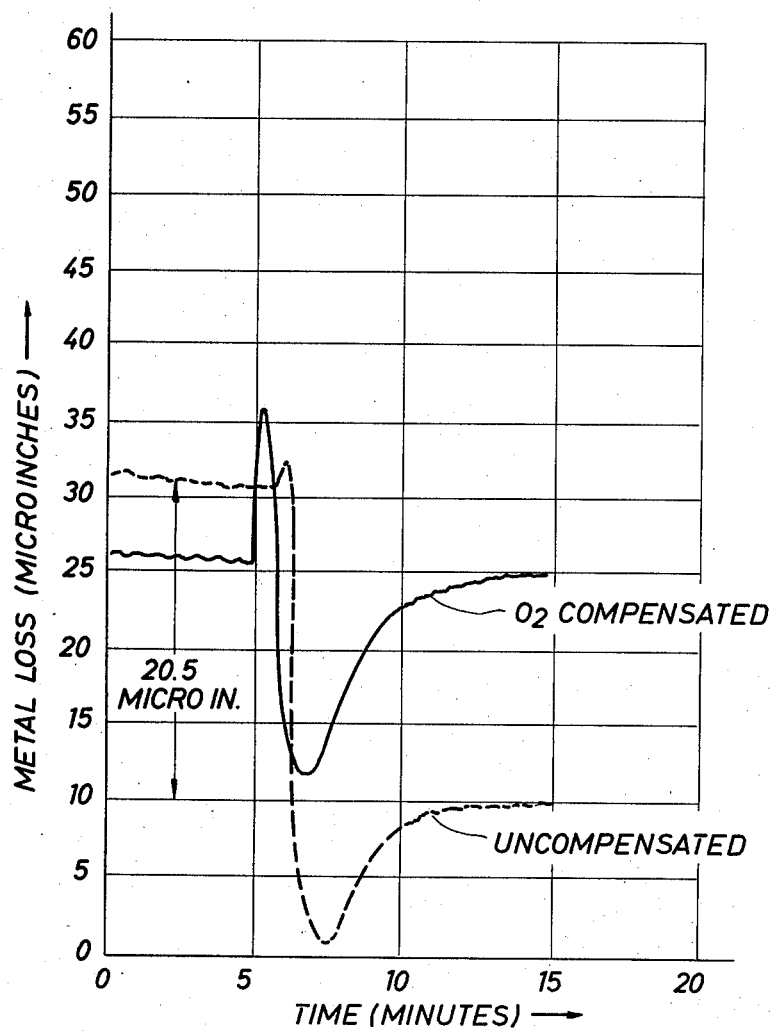
FIG. 3 is a graphic representation plotting instantaneous corrosion against time for a compensated and an uncompensated corrosion measurement system.

An example of the improvement possible with the temperature compensating network of the present invention is shown in FIG. 3. The dashed curve shows the original instrument output signal as resistance element temperatures were increased by 20° C. An apparent probe thickening of 20.5 micro inches results, which is equivalent to a −180 MPY rate for one hour's corrosion. The solid curve shows the net resulting signal 02 with very little offset after the short-term temperature transients have settled out.

It should be apparent from the foregoing detailed description that the primary object of the invention may be satisfied even though certain intermediate signal processing steps are omitted. For instance, it may not become necessary to provide isolation amplifiers or further amplification if the sampling point for reference signal 9 of FIG. 1 is chosen so that its base reference is equivalent to that of output 01.

What we claim is:

1. Apparatus for compensating for temperature variations in an electrical resistance corrosion measurement system, wherein at least two electrically conducting resistance elements are disposed in a corrosive atmosphere, a first element being the active element, a second element being a reference element, said first and second elements being electrically connected so that a supplied signal from electrical instrumentation induces a measurable signal across each resistance element, said measurable signal across said active element being proportional to corrosion of said active element, said measurable signal across said reference element being substantially proportional to the temperature of said corrosive atmosphere, said apparatus comprising:
    means for sampling a signal which varies with changes in temperature to provide a reference signal;
    means for converting said reference signal to the same base reference as the base reference of the uncompensated system output to provide a converted signal;
    means for transforming said converted signal to an equivalent signal form of the uncompensated system output to provide an equivalent signal; and
    means for combining said equivalent signal and said uncompensated system output whereby the degrading effect of all temperature variations in said corrosion measuring system is eliminated from the net resulting output.

2. Apparatus according to claim 1, wherein said supplied signal is a current signal;
    said reference signal is a voltage signal; and
    said base reference is ground potential of said system output.

3. Apparatus according to claim 2, wherein a resistance is serially connected to said electrical instrumentation in a current line for providing a sampling point for said reference signal, current in said current line being directly proportional to said supplied current.

4. Apparatus according to claim 1, wherein the means for converting said reference signal to said base reference comprises an isolation amplifier.

5. Apparatus according to claim 1, wherein the means for transforming said converted signal to said equivalent signal form comprises at least one emplifier.

6. Apparatus according to claim 1, wherein the means for combining said equivalent signal and said uncompensated system output comprises a subtractor circuit for subtracting said equivalent signal from said uncompensated system output.

7. Method of compensating for temperature variations in an electrical resistance corrosion measuring system, wherein at least two electrically conducting resistance elements are disposed in a corrosive atmosphere, a first element being the active element, a second element being a reference element, said first and second elements being serially connected so that a supplied signal induces a measurable signal across each resistance element to produce an uncompensated system output, said measurable signal across said active element being proportional to corrosion of said active element, said measurable signal across said reference element being substantially proportional to the temperature of said corrosive atmosphere, said method comprising:
    monitoring said supplied signal to provide a monitored supply signal;
    sampling a signal proportional to corrosive atmosphere temperature for ascertaining temperature variations to provide a reference signal;
    electrically combining said monitored supply signal and said reference signal into a composite signal such that all variations of said composite signal corresponds to a temperature variations;
    converting said composite signal into a form equivalent to said system output to provide an equivalent signal; and
    electrically subtracting said equivalent signal from said system output suchh that the net resulting output is fully compensated for temperature variations.

8. Method according to claim 7 wherein said supplied signal is a current signal; said measurable signal is a voltage signal; and said reference signal is a voltage signal.

9. Method according to claim 8 wherein said supplied signal is varied such that said measurable signal across said reference element is held constant during temperature variations;

said reference signal which is proportional to said varying supply signal is isolated electrically from the sampling point to provice an isolated voltage;

said isolated voltage is amplified electrically to a a level equivalent to said system output to provide an amplified voltage; and said amplified voltage and said system output are electrically passed through a subtractor circuit such that the net resulting output is fully compensated for temperature variations.

10. Apparatus for compensating for temperature variations in a corrosion measuring system comprising:

a plurality of resistance elements disposed in a corrosive atmosphere, operatively connected to electrical instrumentation means for providing generated signals in said resistance elements;

electrical measuring means operatively connected to said resistance elements for measuring changes in said generated signals across said resistance elements to provide measured signals, said changes due at least in part to corrosion of said resistance elements, and at least in part to temperature variations of said corrosive atmosphere;

electrical means connected to said electrical measuring means for combining said measured signals across said resistance elements to provide an uncompensated system output;

electrical sampling means operatively connected to said electrical instrumentation means for sampling an electrical signal which is proportional to temperature variations of said corrosive atmosphere to provide a reference signal; and a subtractor circuit electrically said uncompensated system output and said reference signal such that the net resulting output is independent of fluctuation due to temperature variations.

11. Apparatus according to claim 10, wherein said generated signals in said resistance elements are induced by a current signal supplied by said electrical instrumentation, and said current signal varies proportionately to temperature variations of said corrosive atmosphere.

12. Apparatus according to claim 11, wherein said electrical sampling means comprises a resistance serially disposed in a current line of said electrical instrumentation, current in said current line being directly proportional to said current signal.

13. Apparatus according to claim 10, including means for amplifying said reference signal to the equivalent signal level of said corrosion system output.

14. Apparatus according to claim 10, including an isolation amplifier for electrically isolating said reference signal from the sampling point for obtaining said reference signal in said electrical instrumentation.

15. Method of increasing the time resolution of a corrosion measuring system, wherein at least two electrically conducting resistance elements are disposed in a corrosive atmosphere, a first element being the active element, a second element being a reference element, said first and second elements being serially connected, a signal supplied from remote electrical instrumentation inducing a measurable signal across each resistance element, said measurable signals resulting in a net corrosion system signal output which is proportional to the corrosion of said active element, said method comprising the steps of:

utilizing said reference element as an electrical resistance thermometer to produce a corresponding temperature signal;

combining said temperature signal with said measurable signal across said active element to compensate for all temperature variations of said corrosive atmosphere;

providing a thermostatically controlled environment for said electrical instrumentation to maintain a constant temperature therein for eliminating ambient temperature effects on said electrical instrumentation;

providing ratio frequency filtering for eliminating interference to said electrical instrumentation caused by extraneous signals;

providing multi-stage input power regulation to said electrical instrumentation for eliminating undesirable corrosion system output variations due to fluctuation of instrumentation input power; and integrating said net corrosion system signal output for eliminating fluctuations in said last-mentioned signal due to short-term thermal transients.

16. Apparatus for compensating for temperature variations in a corrosion measuring system comprising:

one or more resistance elements disposed in a corrosive atmosphere, operatively connected to electrical instrumentation means for providing generated signals in said resistance elements;

electrical measuring means operatively connected to said resistance elements for measuring changes in said generated signals across said resistance elements to provide measured signals, said changes due at least in part to corrosion of said resistance elements, and at least in part to temperature variations of said corrosive atmosphere;

electrical means connected to said electrical measuring means for combining said measured signals across said resistance elements to provide an uncompensated system output;

temperature sensing means for providing an electrical signal which is proportional to temperature variations of said corrosive atmosphere to provide a reference signal; and electrical means for combining said uncompensated system output and said reference signal such that the net resulting output is independent of fluctuatiom due to temperature variations.

* * * * *